United States Patent [19]
Tropsha et al.

[11] Patent Number: 6,054,188
[45] Date of Patent: Apr. 25, 2000

[54] NON-IDEAL BARRIER COATING ARCHITECTURE AND PROCESS FOR APPLYING THE SAME TO PLASTIC SUBSTRATES

[75] Inventors: Yelena G. Tropsha, Chapel Hill; David A. Martin, Raleigh; Kevin D. Mar; Jane C. Graper, both of Durham, all of N.C.; Jamshed B. Ghandhi, San Carlos, Calif.

[73] Assignee: Becton Dickinson and Company, Franklin Lakes, N.J.

[21] Appl. No.: 09/366,291

[22] Filed: Aug. 2, 1999

[51] Int. Cl.$^7$ ................................ C08F 2/46; C08J 7/18; H05H 1/00
[52] U.S. Cl. ................ 427/488; 427/255.29; 427/255.6; 427/255.7; 427/294; 427/407.1; 427/419.3; 427/574; 427/576; 427/579
[58] Field of Search ........................... 427/255.29, 255.6, 427/255.7, 294, 407.1, 419.3, 488, 574, 576, 579

[56] References Cited

U.S. PATENT DOCUMENTS

| | | |
|---|---|---|
| 5,545,375 | 8/1996 | Tropsha et al. . |
| 5,665,280 | 9/1997 | Tropsha . |
| 5,683,771 | 11/1997 | Tropsha . |
| 5,686,157 | 11/1997 | Harvey et al. . |
| 5,691,007 | 11/1997 | Montgomery . |
| 5,716,683 | 2/1998 | Harvey et al. . |
| 5,738,920 | 4/1998 | Knors . |

FOREIGN PATENT DOCUMENTS

| | | |
|---|---|---|
| 2161362 | 10/1995 | Canada . |
| 719877A1 | 12/1994 | European Pat. Off. . |

OTHER PUBLICATIONS

Surface & Coatings Technology 80 (1996) pp. 200–202, M. Walther, M. Heming, M. Spallek, Schott Glaswerke Research Center, 10 Postfach 24 80 Mainz 55014, Germany Entitled: Multilayer barrier coating system produced by plasma–impulese chemical vapor deposition (PICVD).

*Primary Examiner*—Bernard Pianalto
*Attorney, Agent, or Firm*—Nanette S. Thomas, Esq.

[57] ABSTRACT

The present invention is a non-ideal barrier coating composition and the method for applying the coating composition to substrates. The non-ideal barrier coating is useful for providing an effective barrier against gas permeability in containers and for extending shelf-life of containers, especially plastic evacuated blood collection devices.

14 Claims, 1 Drawing Sheet

NON-IDEAL BARRIER COATING ARCHITECTURE AND PROCESS FOR APPLYING THE SAME TO PLASTIC SUBSTRATES

BACKGROUND OF THE INVENTION

1. Field of the Invention

This invention relates to a non-ideal barrier coating sequence architecture and a method for depositing the non-ideal barrier coating sequence architecture to plastic substrates for improving the effective barrier of plastic substrates against gas and water permeability.

2. Description of the Related Art

With the increased emphasis on the use of plastic medical products, a special need exists for improving the barrier properties of articles made of polymers.

Such medical products that would derive a considerable benefit from improving their barrier properties include, but are not limited to, collection tubes and particularly those used for blood collection. Additionally, such improvements of barrier properties of articles made of polymers can also have applications with respect to food, cosmetics and the like.

With respect to, for example blood collection tubes, they require certain performance standards to be acceptable for use in medical applications. Such performance standards include the ability to maintain greater than about 90% original draw volume over a one year period, to be radiation sterilizable and to be non-interfering in tests and analysis.

Therefore, a need exists to improve the barrier properties of articles made of polymers and in particular plastic evacuated blood collection tubes wherein certain performance standards would be met and the article would be effective and usable in medical applications.

SUMMARY OF THE INVENTION

The present invention is a non-ideal composite barrier coating sequence architecture, a plastic substrate comprising the non-ideal barrier coating sequence architecture and a method for depositing the non-ideal barrier coating sequence architecture on a plastic substrate. The non-ideal barrier coating sequence architecture desirably comprises a sequence of organic and inorganic materials whereby the barrier performance of the non-ideal barrier coating sequence composition as a whole is greater than the lamination of each individual material in the whole composition.

Most preferably, the sequence of the materials may be expressed as follows:

Sequence=inorganic material+organic material+inorganic material.

Desirably, the inorganic material is a reactive blend of a monomer gas and an oxidizer gas.

Desirably, the inorganic material is a metal oxide, such as a silicon oxide based composition, such as $SiO_x$ wherein x is from 1.0 to about 2.5; or an aluminium oxide based composition. Most preferably, the inorganic material is $SiO_x$.

Preferably, the silicon oxide based material is substantially dense and vapor-impervious and is desirably derived from volatile organosilicon compounds. Preferably, the thickness of the silicon oxide based material is about 100 to about 2,000 Angstroms (Å) and most preferably from about 500 to about 1,000 Å. A material above 5,000 Å may crack and therefore be ineffective as a barrier.

Desirably, the organic material is a polymer material and is preferably formed over the inorganic material.

Preferably, the organic material is formed by a monomer gas. Most preferably, the monomer gas is hexamethyldisiloxane (HMDSO), trimethylsilane (TMSO), or vinyltrimethoxysilane.

Preferably, the thickness of the organic material is about 10 to about 10,000 Angstroms Å and most preferably about 200 to about 4,000 Å.

Most preferably, the apparatus for depositing the non-ideal barrier coating sequence architecture on a substrate comprises:

(a) a vacuum tight chamber;
(b) means for delivering a monomer gas to said chamber;
(c) means for delivering an oxidizer gas to said chamber;
(d) means for applying radio frequency power to said chamber;
(e) electrodes; and
(f) means for creating and maintaining a vacuum inside said chamber.

Most preferably, the method for depositing the non-ideal barrier coating sequence architecture on a substrate, comprises the following steps:

(a) positioning said substrate in the chamber;
(b) evacuating the chamber to below 5 mTorr
(c) delivering a first monomer gas to said chamber;
(d) delivering an oxidizer gas to said chamber;
(e) delivering a first radio frequency electrical current to the electrodes;
(f) depositing a first inorganic material on said substrate;
(g) evacuating said chamber to below 5 m Torr;
(h) delivering a second monomer gas to said chamber;
(i) delivering a second radio frequency electrical current to the electrodes;
(j) depositing an organic material on said first inorganic material;
(k) repeating steps (b)–(f) to deposit a second inorganic material on the organic material.

Preferably, the first monomer gas is delivered to the chamber at about 0.5 sccm to about 10 sccm and most preferably at about 2.5 sccm.

Preferably, the first monomer gas is hexamethyldisiloxane (HMDSO), trimethylsilone (TMSO), or tetraethoxysilane (TEOS) and most preferably HMDSO.

Preferably, the oxidizer gas is delivered to the chamber at about 25 sccm to about 100 sccm and most preferably at about 70 sccm.

Preferably, the oxidizer gas is oxygen, nitrous oxide or air.

Preferably, the second monomer gas is delivered to the chamber at about 5 sccm to about 18 sccm and most preferably at about 8 sccm.

Preferably, the second monomer gas is hexamethyldisiloxane (HMDSO), trimethylsilane (TMSO) or vinyltrimethylsilane and most preferably HMDSO.

Preferably, the radio frequency is from about 0.4 to about 75 $MH_z$ and from about 0.13 to about 0.63 watts/cm$^2$. Most preferably, the radio frequency is about 5 to about 25 $MH_z$ and about 0.38 to about 0.50 watts/cm$^2$.

Plastic substrates coated with the non-ideal barrier coating sequence of the present invention are able to maintain substantially far better vacuum retention, than substrates coated with only an oxide material. Most notably is the clarity of the non-ideal barrier coating sequence of the present invention and its durability to substantially withstand resistance to impact and abrasion.

Preferably, the substrate of the present invention is a blood collection device. The blood collection device can be either an evacuated blood collection tube or a non-evacuated blood collection tube. The blood collection tube is desirably made of polyethylene terephthalate (PET), polypropylene (PP), polyethylene napthalate (PEN), polycarbonate (PC) or copolymers thereof.

Preferably, the non-ideal barrier coating sequence and method of depositing the sequence of the present invention provides a coating that is transparent, translucent or colorless appearance and may be subjected to a sterilization process for medical devices.

Most notably an advantage of the present invention is the "one-box" process that provides a time and cost efficient means of applying a non-ideal barrier coating to a substrate.

The non-ideal barrier coating sequence of the present invention provides a reduction in permeation greater than is expected by standard permeation theory. Permeation thermodynamics demonstrates that the non-ideal barrier coating sequence of the present invention exhibits a more nearly "glass-like" property than a single-layer $SiO_x$ barrier coating sequence. Therefore, the non-ideal barrier coating sequence of the present invention provides an unpredicted barrier system.

It has also been found that the non-ideal barrier coating sequence of the present invention does not exhibit true laminate properties in accordance with the laminate equation.

When two or more different barrier films are stacked, the permeation of small molecules through the multilayer laminate is generally described by the laminate equation:

$$(\Pi_{12}) = (\Pi_1^{-1} + \Pi_2^{-1})^{-1}$$

where $\pi_1$, is the permeation rate through component layer 1, $\pi_2$, is the permeation rate through component layer 2 and $\pi_{12}$, is the permeation rate through the laminate of components 1 and 2. When the permeance of the individual components is known the permeance of the total layer laminate of those components can be calculated and predicted.

However, the transport rate of permeants through the non-ideal barrier coating sequence of the present invention is lower than the permeation rate predicted by the laminate equation. Therefore the non-ideal barrier coating sequence of the present invention is a non-ideal composite with unpredicted transport rate of permeants.

Based on Arrhenious theory, the performance of the non-ideal barrier coating sequence of the present invention is different from predicted laminates because permeation of gases through the non-ideal barrier coating sequence of the present invention requires the expenditure of more thermal energy than would be predicted from the laminate equation.

The laminate equation is therefore modified for the non-ideal barrier coating sequence of the present invention as follows:

$$\Pi_{oi} < (\Pi_o^{-1} + 2\Pi_i^{-1})^{-1}$$

The two inorganic layers are assumed to be identical, each with permeance $\pi_i$ thus with combined permeance of $\pi_i/2$. However, this need not be the case. For example, if the inorganic layers had permeances of $\pi_{i1}$ and $\pi_{i2}$, then the laminate equation is expressed more generally as:

$$\Pi_{oi} < (\Pi_o^{-1} + \Pi_{i1}^{-1} + \Pi_{i2}^{-1})^{-1}$$

where if $\pi_{i1}$ and $\pi_{i2}$ are the same, their sum of inverses may be expressed as $2\pi_i^{-1}$.

Where $\pi_o$ is the permeation rate through the organic material of the sequence, $\pi_i$ is the permeation rate through the inorganic material of the sequence and $\pi_{oi}$ is the permeation rate through the laminate of the organic and inorganic materials. The transport rate of permeants is therefore less than expected from ideal additivity.

It can therefore be concluded that the transport rate of permeants through the non-ideal barrier coating sequence or non-ideal composite of the present invention is not an additive effect. Therefore, non-ideal composites must be discovered for maximum permeance efficiency or performance and not predicted. Furthermore, the permeance properties of a non-ideal composite are not inherent.

When the transmission rate of a permeant, such as oxygen or water, through a barrier structure is obtained at several different temperatures, the thermodynamic energy necessary to transport the permeant completely through the barrier structure is obtained by the Arrhenius equation:

$$\ln Q = \ln Q_0 - \Delta G / RT$$

where $\Delta G$ is the energy necessary to move one mole of permeant molecules through the barrier structure in cal/mole, R is the gas constant in cal/mole–degree, T is temperature in degrees Kelvin, Q is the permeant transmission rate and $Q_o$ is a constant unique to the structure. In practice, the transmission rate Q for oxygen transport through the barrier structure is obtained at several temperatures. Then the natural log of the transmission rate obtained at each temperature versus the reciprocal of each temperature is plotted. The slope of the resultant linear plot is the quantity $-\Delta G/R$, from which $\Delta G$ is obtained.

It has also been found that the non-ideal barrier coating sequence of the present invention results in the expenditure of more thermal energy ($\Delta G$) than that of any of the components of the composition; $\Delta G_T > \Delta G_A$ and $\Delta G_B$, where T is the non-ideal barrier coating sequence and A and B are the organic and inorganic components of the non-ideal barrier coating sequence. In contrast, a laminate or ideal composite will have a $\Delta G_T = \Delta G_A$ or $\Delta G_B$, whichever component (A or B) has the lowest permeance.

DETAILED DESCRIPTION

Figure 1:
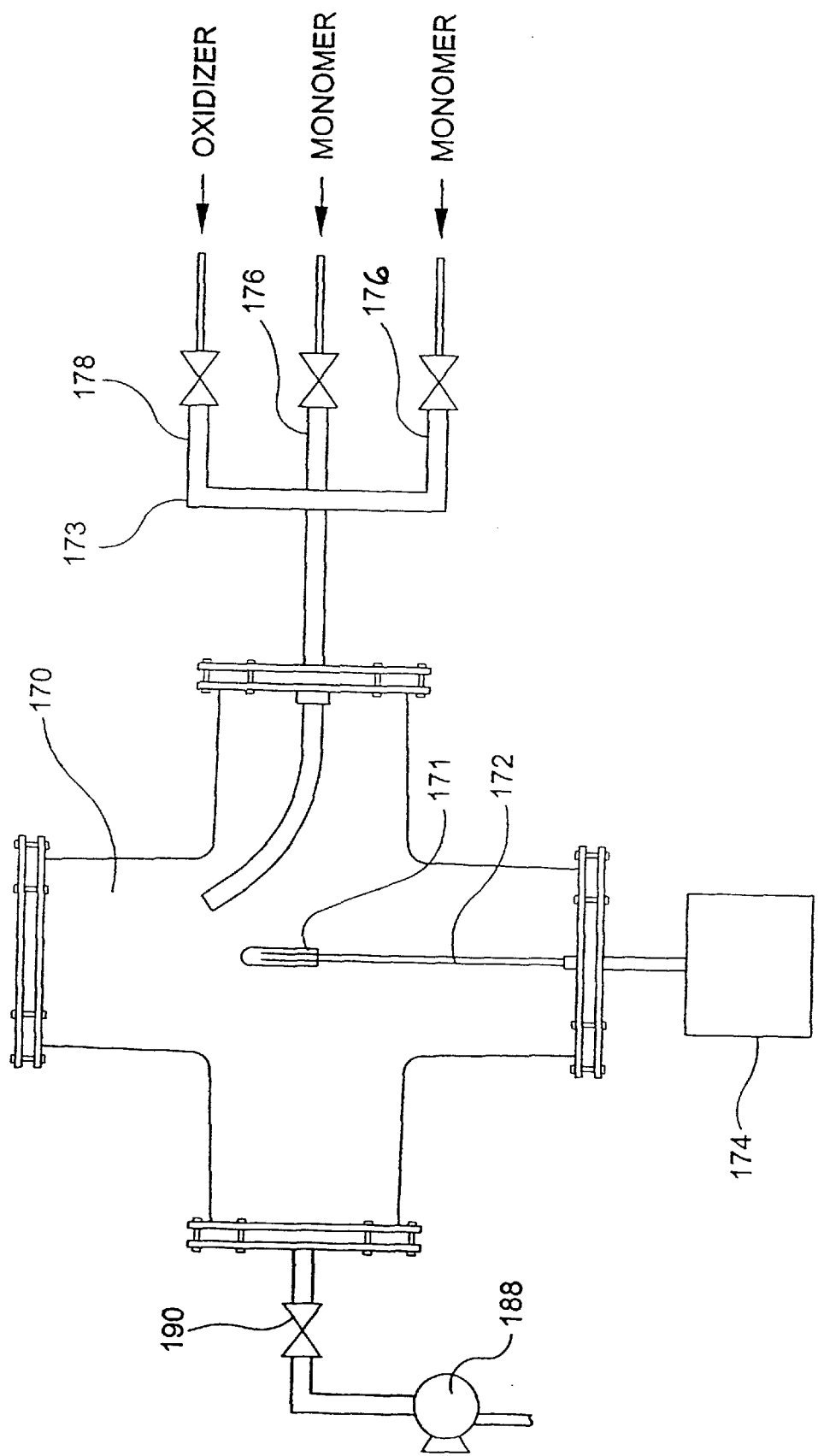
FIG. 1 illustrates the apparatus for plasma enhanced chemical vapor deposition.

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

The preferred embodiment of the present invention is the sequential deposition of inorganic and organic material by plasma enhanced chemical vapor deposition (PECVD) onto a plastic substrate. Most preferably, the entire process is conducted in a vacuum chamber.

The plastic substrate used in the present in the present invention may be any substrate which would benefit from reduced gas and/or water vapor transmission in its end use. A representative but not limiting list of such substrates includes films, films for packaging, containers such as bottles, medical devices such as syringes, tubes, tubing and vials. Most preferably, soft drink containers and medical devices would benefit from reduced gas and/or vapor transmission.

It is within the purview of this invention that the sequential deposition of the materials may be formed by radio frequency discharge, direct or dual ion beam deposition, sputtering or plasma enhanced chemical vapor deposition, as described in U.S. Pat. Nos. 4,698,256, 4,809,298, 5,055,318 and 5,691,007, the disclosures of which are herein incorporated by reference.

The non-ideal barrier coating sequence preferably comprises multiple materials expressed as follows:

Sequence=inorganic material+organic material+inorganic material.

Referring to FIG. 1, the apparatus for depositing materials onto a plastic substrate comprises an enclosed reaction chamber 170 in which a plasma is formed and in which a substrate or tube 171, is placed on electrodes 172. One or more gases can be supplied to the reaction chamber by a gas supply system 173. An electric field is created by a power supply 174.

The reaction chamber can be of an appropriate type to perform any of the plasma-enhanced chemical vapor deposition (PECVD) or plasma polymerization process. Furthermore, the reaction chamber may be used so that one or more substrates may be coated simultaneously within the chamber.

The pressure of the chamber is controlled by a pump 188 connected to chamber 170 by a valve 190.

The substrate to be coated is loaded into chamber 170 onto electrodes 172. For purposes of illustration, the substrate to be coated is a tube or container. The pressure of the chamber is reduced to about 5 m Torr by mechanical pump 188. The operating pressure of the chamber is about 50 to about 2,000 mTorr for a PECVD or plasma polymerization process and is achieved by flowing the process gases, as needed into the chamber through monomer inlet 176 and/or oxidizer inlet 178.

A radio frequency (RF) electrical current from supply 174 is then applied to the electrodes at a frequency of about 0.4 to 100 $MH_z$ and a power per electrode area of about 0.1 to 2.0 watts/cm$^2$ depending upon the number and proximity of the electrodes to generate a plasma and finally an inorganic or organic coating on the substrate.

Examples of suitable oxidizers useful for the gas stream in the plasma deposition method are oxygen, nitrous oxide, and air.

Examples of suitable organosilicon compounds useful for the gas stream in the plasma deposition methods are liquid or gas at about ambient temperature and when volatilized have a boiling point about 0° C. to about 150° C. and include dimethylsilane, trimethylsilane, diethylsilane, propylsilane, phenylsilane, hexamethyldisilane, 1,1,2,2-tetramethyldisilane, bis (trimethylsilyl) methane, bis (dimethylsilyl) methane, hexamethyldisiloxane, vinyl trimethoxy silane, vinyl triethyoxysilane, ethylmethoxysilane, ethyltrimethoxysilane, divinyltetramethyldisiloxane, hexamethyldsilazane divinylhexamethyltrisiloxane, trivinylpentamethyltrisiloxazane, tetraethoxysilane and tetramethoxysilane.

Among the preferred organosilicons are 1,1,3,3-tetramethyldisiloxane, trimethylsilane, hexamethyldisiloxane, vinyltrimethylsilane, methyltrimethoxysilane, vinyltrimethoxysilane and hexamethyldisilazane. These preferred organosilicon compounds have boiling points of 71° C., 55.5° C., 102° C., 123° C. and 127° C. respectively.

EXAMPLE 1

Method for Applying a Non-ideal, Barrier Coating Sequence to Substrates

A non-ideal barrier coating sequence and comparative coatings were applied to PET tubes using the apparatus as described in FIG. 1, with varying conditions.

The tubes were positioned in the vacuum chamber, as shown in FIG. 1 on electrodes. The chamber was evacuated to about 0.5 m Torr. Organic and inorganic coatings were applied to the tubes in various configurations. An organic coating of HMDSO was deposited whereby a monomer was delivered to the chamber with a specific power supplied to the electrodes. An inorganic coating of $SiO_x$ was deposited whereby a monomer and an oxidizer were delivered to the chamber at a specific pressure and power supplied to the electrodes.

The system parameters used for the various sequences and controls are listed in Tables 1–2.

EXAMPLE 2

Behavior Characteristics of Non-ideal Composite Compositions

PET tubes were prepared in accordance with Example 1 above and then the following characteristics and properties were evaluated and the results are reported in Tables 1–3.
(i) Arrhenius relationship analysis:

When the transmission rate of a permeant, such as oxygen or water, through as barrier structure is obtained at several different temperatures, the thermodynamic energy necessary to transport the permeant completely through he barrier structure is obtained by the Arrhenius equation:

$$\ln Q = \ln Q_0 - \Delta G / RT$$

where $\Delta G$ is the energy necessary to move one mole or permeant molecules through the barrier structure in cal/mole, R is the gas constant in cal/mole–degree, T is temperature in degrees Kelvin, Q is the permeant transmission rate and $Q_o$ is a constant unique to the structure. In practice, the transmission rate Q for oxygen transport through the barrier structure is the permeance $\pi$, obtained at several temperatures. Then the natural log of the transmission rate obtained at each temperature versus the reciprocal of each temperature is plotted. The slope of the resultant linear plot is $-\Delta G/R$, from which $\Delta G$ is obtained.

These data are obtained at several defined temperatures, using the same equipment as described above. The resulting permeance data ($\pi$) are then treated by the Arrhenius equation, and $\Delta G$ values for the laminate are compared to $\Delta G$ values obtained for the components of the laminate. An ideal laminate system has a $\Delta G$ equivalent to that of the component with the best barrier characteristics. A non-ideal system has a $\Delta G$ greater than that of either component.
(ii) Oxygen permeance (OTR):

Tube samples were tested for oxygen permeance (OTR) using MOCON Ox-TRAN 1,000 (sold by Modem Controls, Inc., 7500 Boone Avenue N., Minneapolis, Minn. 55428). A package adapter was used for mounting the tubes in a manner that allowed the outside of the tube to be immersed in a 100% $O_2$ atmosphere while the inside of the tube was flushed with a nitrogen carrier gas. The tubes were then tested at 50% R.H. The tubes were allowed to equilibrate for 2–14 days before a steady state permeability was determined The results are reported in Table 1.

(iii) Water Vapor Transmission Rate (WVTR):

Tubes were filled with a 2 ml of distilled water, close with a rubber stopper, and placed into an oven at 40° C., 50% R.H. The tubes were then weighed once per week for 4 months. The water vapor transmission rates were then calculated based on the equilibrium water loss per day. The results are reported in Table 2.

(iv) Air permeance through tubes.

To measure air permeance through tubes, the apparatus as described used in U.S. Pat. No. 5,792,940 was used and has been incorporated by reference.

TABLE 1

GAS BARRIER CHARACTERISTICS OF TUBES

| Sample Description | Measured Oxygen Permeance ($10^{-10}$ moles/ $m^2 \cdot$ sec atm @ 40° C., 50% R.H.) | Theoretical Oxygen Permeance ($10^{-10}$ moles/ $m^2 \cdot$ sec atm @ 40° C., 100% R.H.) |
|---|---|---|
| PET, control | 67.8 | — |
| PET/SiO$_x$ (i) | 34 | — |
| PET/HMDSO | 67.8 | — |
| PET/HMDSO/SiO$x$ | 34 | 34 |
| PET/SiO$_x$/HMDSO/SiO$_x$ (i) (ii) | 14.5 | 22.7 |

(i) SiO$_x$ coating was deposited using the following conditions:
Power = 130 watts
Pressure = 120 mTorr
HMDSO flow = 2.5 sccm
$O_2$ flow = 70 sccm
(ii) HMDSO coating was deposited using the following conditions:
Power = 150 watts
Pressure = 120 mTorr
HMDSO flow = 8 sccm

TABLE 2

WATER BARRIER CHARACTERISTICS OF TUBES (Example 5) WATER VAPOR TRANSMISSION

| Sample Description | Measured Water Vapor Permeance Rate ($10^{-7}$ moles/ $m^2 \cdot$ sec @ 40° C., 50% R.H.) | Theoretical Water Vapor Permeance ($10^{-7}$ moles/ $m^2 \cdot$ sec @ 40° C., 50% R.H.) |
|---|---|---|
| PET tube, control | 369 | — |
| PET/SiO$_x$ (i) | 160.4 | — |
| PET/HMDSO/SiO$_x$ (i) (ii) | 184.5 | 160.4 |
| PET/SiO$_x$/HMDSO (i) (ii) | 98.4 | 160.4 |
| PET/SiO$_x$/HMDSO/SiO$_x$ (i) (ii) | 41.8 | 102.2 |
| PET/HMDSO (ii) | 369 | 369 |

(i) SiO$_x$ coating was deposited using the following conditions:
Power = 130 watts
Pressure = 120 mTorr
HMDSO flow = 2.5 sccm
$O_2$ flow = 70 sccm
(ii) HMDSO coating was deposited using the following conditions:
Power = 150 watts
Pressure = 120 mTorr
HMDSO flow = 8 sccm

TABLE 3

ACTIVATION ENERGY FOR AIR TRANSPORT THROUGH TUBES

| Sample Description | $G_{air}$(kcal/mole) |
|---|---|
| PET | 9 |
| PET/SiO$_x$ | 9 |
| PET/HMDSO | 9 |
| PET/SiO$_x$/HMDSO/ SiO$_x$ | 29 |

What is claimed:

1. A method for depositing onto a substrate a non-ideal barrier coating sequence comprising an inorganic material and organic materials comprising the steps of:

(a) providing a vacuum tight chamber, means for delivering a monomer gas to said chamber, means for delivering an oxidizer gas to said chamber, means for applying radio frequency power to said chamber, means for creating and maintaining a vacuum inside said chamber and electrodes;

(b) positioning said substrate in said chamber;

(c) evacuating said chamber to below 50 mTorr;

(d) delivering a first monomer gas to said chamber;

(e) delivering an oxidizer gas to said chamber;

(f) delivering a first radio frequency electrical current to said electrodes;

(g) depositing an inorganic material on said substrate;

(h) evacuating said chamber to below 50 mTorr;

(i) delivering a second monomer gas to said chamber;

(j) delivering a second radio frequency electrical current to said electrodes;

(k) depositing an organic material on said inorganic material; and (l) repeating steps (c)–(f) above; and (m) depositing an inorganic material on said organic material.

2. The method of claim 1, wherein said first monomer gas is delivered to said chamber at about 0.5 sccm to about 10 sccm.

3. The method of claim 1, wherein said first monomer gas is hexamethyldisiloxane (HMDSO), trimethylsilane (TMSO), or tetraethoxysilane (TEOS).

4. The method of claim 1, wherein said oxidizer gas is delivered to said chamber at about 25 sccm to about 70 sccm.

5. The method of claim 1, wherein said oxidizer gas is oxygen, nitrous oxide or air.

6. The method of claim 1, wherein said second monomer gas is delivered to said chamber at about 5 sccm to about 18 sccm.

7. The method of claim 1, wherein said second monomer gas is hexamethyldisiloxane (HMDSO), trimethylsilane (TMSO) or tetraethoxysilane (TEOS).

8. The method of claim 1, wherein said inorganic coating is a metal oxide.

9. The method of claim 8, wherein said metal oxide is a silicon oxide based composition or an aluminum oxide based composition.

10. The method of claim 9, wherein said metal oxide is a silicon oxide based composition.

11. The method of claim 1, wherein said organic material is formed by plasma polymerization of a volatile organo-silicon compound.

12. The method of claim 1, wherein said organic material is formed by plasma polymerization of hexamethyldisiloxane.

13. The method of claim 1, wherein the permeation rate of the lamination of said organic and inorganic materials ($\pi_{oi}$) of said sequence, is less than the inverse of the sum of the inverse of the permeation rate through said two inorganic materials ($\pi_{i1}^{-1}+\pi_{i2}^{-1}$) of said sequence and the inverse of the permeation rate through said organic material ($\pi_{o}^{-1}$) of said sequence.

14. The method of claim 13, wherein said permeation rate of said lamination of said organic and inorganic materials is not an additive effect.

* * * * *